(12) United States Patent
Kechele

(10) Patent No.: US 11,925,738 B2
(45) Date of Patent: Mar. 12, 2024

(54) HEATER/COOLER FOR AN OXYGENATOR

(71) Applicant: LivaNova Deutschland GmbH, Munich (DE)

(72) Inventor: Marco Kechele, Munich (DE)

(73) Assignee: LivaNova Deutschland GmbH, Munich (DE)

( * ) Notice: Subject to any disclaimer, the term of this patent is extended or adjusted under 35 U.S.C. 154(b) by 319 days.

(21) Appl. No.: 16/753,913

(22) PCT Filed: Sep. 26, 2018

(86) PCT No.: PCT/EP2018/076081
§ 371 (c)(1),
(2) Date: Apr. 6, 2020

(87) PCT Pub. No.: WO2019/068530
PCT Pub. Date: Apr. 11, 2019

(65) Prior Publication Data
US 2020/0261636 A1 Aug. 20, 2020

(30) Foreign Application Priority Data
Oct. 6, 2017 (DE) .................... 10 2017 2177 82.9

(51) Int. Cl.
*A61M 1/36* (2006.01)
*A61M 1/16* (2006.01)

(52) U.S. Cl.
CPC ........ *A61M 1/1698* (2013.01); *A61M 1/1629* (2014.02); *A61M 1/3623* (2022.05);
(Continued)

(58) Field of Classification Search
CPC .............. A61M 1/1629; A61M 1/1698; A61M 1/3666; A61M 2202/047; A61M 2205/36;
(Continued)

(56) References Cited

U.S. PATENT DOCUMENTS

| 4,559,999 A | 12/1985 | Servas et al. |
| 5,125,069 A | 6/1992 | O'Boyle |

(Continued)

FOREIGN PATENT DOCUMENTS

| DE | 102014116601 A1 * | 5/2016 | .......... A61M 1/1698 |
| DE | 102014116601 A1 | 5/2016 | |

(Continued)

OTHER PUBLICATIONS

Machine Translation of DE 102014116601 obtained from Google Patents on Mar. 25, 2022 (Year: 2022).*

(Continued)

*Primary Examiner* — Benjamin J Klein
(74) *Attorney, Agent, or Firm* — Seager, Tufte & Wickhem LLP

(57) ABSTRACT

The present disclosure relates to a system for extracorporeal blood circulation, including an oxygenator which includes a heat exchanger configured for warming or cooling blood in extracorporeal blood circulation of a patient, and a heater/cooler configured for exchanging a quantity of heat with the heat exchanger, wherein the heater/cooler includes an thermoelectric heater/cooler and wherein the heater/cooler (14) is connected to the heat exchanger (11) by a thermal connecting element (15).

10 Claims, 2 Drawing Sheets

(52) U.S. Cl.
CPC ............... *A61M 2202/047* (2013.01); *A61M 2205/3673* (2013.01)

(58) Field of Classification Search
CPC .... A61M 2205/3606; A61M 2205/366; A61M 2205/3673
See application file for complete search history.

(56) References Cited

U.S. PATENT DOCUMENTS

| | | | |
|---|---|---|---|
| 6,045,752 A | 4/2000 | Elgas | |
| 7,841,189 B2 | 11/2010 | Poch | |
| 2003/0045917 A1 | 3/2003 | Noda et al. | |
| 2012/0193289 A1 | 8/2012 | Cloutier et al. | |
| 2013/0280692 A1* | 10/2013 | Gourlay | A61M 1/262 422/46 |
| 2014/0172050 A1 | 6/2014 | Dabrowiak | |
| 2014/0358201 A1 | 12/2014 | Scott et al. | |
| 2017/0216509 A1 | 8/2017 | Bellini | |
| 2017/0267907 A1 | 9/2017 | Knott et al. | |

FOREIGN PATENT DOCUMENTS

| | | |
|---|---|---|
| WO | 2012/013925 A2 | 2/2012 |
| WO | 2012/017417 A2 | 2/2012 |
| WO | 2016/195651 A1 | 12/2016 |
| WO | 2017/042319 A1 | 3/2017 |

OTHER PUBLICATIONS

International Search Report and Written Opinion received for PCT Patent Application No. PCT/EP2017/075473, dated Jun. 7, 2018, 14 pages.

International Search Report and Written Opinion received for PCT Patent Application No. PCT/EP2018/076081, dated Mar. 13, 2019, 15 pages.

* cited by examiner

US 11,925,738 B2

HEATER/COOLER FOR AN OXYGENATOR

TECHNICAL FIELD

The present disclosure relates to a device with the aid of which an oxygenator, e.g. an oxygenator of a heart-lung machine, is able to warm or cool blood in a patient's extracorporeal blood circulation.

BACKGROUND

Oxygenators are devices used for extracorporeal oxygenation of blood. Such oxygenators are used e.g. in heart-lung machines or in extracorporeal membrane oxygenation (ECMO) devices. Commonly used devices of this type are membrane oxygenators by means of which embolisms can reliably be avoided to a very large extent. With the aid of gas mixers and flow meters the transfer of oxygen and carbon dioxide can be controlled reliably.

In the oxygenator, the blood in a patient's extracorporeal blood circulation is not only oxygenated but also warmed or cooled. In particular, hypothermia is very important for reducing the oxygen consumption of the patient's organism. For warming or cooling the blood in the extracorporeal blood circulation, the oxygenator comprises a heat exchanger. A heat exchanging medium flows through the heat exchanger and transfers a heat quantity to the blood (blood warming) or absorbs a heat quantity from the blood (blood cooling). The heat exchanging medium is usually supplied to the heat exchanger by a pump unit and, after heat exchange with the blood has taken place, it is discharged from the heat exchanger by another pump unit. The heat exchanging medium, e.g. water, is previously heated or cooled in a heater/cooler (a hypothermia device) before it is conducted to the heat exchanger. Due to its size and complex structure, the heater/cooler is configured e.g. separately from the heart-lung machine.

The heater/cooler may be contaminated with germs from inside. Hence, there is the risk that equipment and the atmosphere in the operating room may be contaminated and that germs will thus finally enter the patient's blood circuit. Furthermore, the heaters/coolers according to the prior art have a comparatively complex structural design and are thus fault-prone.

Hence, it is an object of the present disclosure to provide for an oxygenator including a heater/cooler, which operates reliably and in a trouble-free and hygienic mode.

SUMMARY

A system for extracorporeal blood circulation is provided, which comprises an oxygenator including a heat exchanger configured for warming or cooling blood of an extracorporeal blood circulation of a patient, and a heater/cooler configured for exchanging a quantity of heat with the heat exchanger of the oxygenator (i.e. for cooling or heating the heat exchanger), wherein the heater/cooler is or comprises a thermoelectric heater/cooler.

Furthermore, the heater/cooler is connected to the heat exchanger by a thermal connecting element (contact element without using any fluid for transferring the heat), whereby a high efficiency of heat exchange between the heat exchanger and the heater/cooler can be achieved and, in particular, the use of a circulating heat exchanging medium, which is conducted through the heat exchanger, can be dispensed with. Hence, pumps for conveying such a heat exchanging medium are not necessary either. The thermal connecting element may comprise a thermally highly conductive material, such as a thermally highly conductive metal.

Here, and in the embodiments described below, the system may be or may comprise a heart-lung machine, an extracorporeal membrane oxygenation (ECMO) device or a minimized extracorporeal circulation (MECC) device. Here, and in the embodiments described in the following, the thermoelectric heater/cooler may comprise at least one Peltier element, in particular, a plurality of Peltier elements which operate in parallel. A plurality of Peltier elements may be provided such that they are connected in series.

It follows that the heater/cooler or the Peltier elements can heat or cool the heat exchanger directly (depending on the selected current direction of the Peltier elements). When the heat exchanger is cooled by the thermoelectric heater/cooler (Peltier elements) to a temperature below the blood temperature, the blood will be cooled, and when the heat exchanger is heated by the thermoelectric heater/cooler (Peltier elements) to a temperature above the blood temperature, the blood will be warmed. It follows that a fully "dry" unit for supplying a quantity of heat to the heat exchanger of the oxygenator can be provided, said unit being almost maintenance-free and allowing a significant reduction of the risk of bacterial contamination (cf. the above description).

Furthermore, it is provided a system for extracorporeal blood circulation, comprising an oxygenator which includes a heat exchanger configured for warming or cooling blood in the extracorporeal blood circulation of the patient, and a reservoir configured for storing a heat exchanging medium and connected to the heat exchanger, wherein the heater/cooler comprises a thermoelectric heater/cooler, and the heater/cooler is connected to the reservoir and configured to heat or cool the heat exchanging medium stored in the reservoir.

It follows that a circulation of a heat exchanging medium (to and from the oxygenator heat exchanger) for cooling or warming a patient's blood may be provided, where the cooling or heating of the heat exchanging medium is accomplished with the aid of the heater/cooler according to the present disclosure.

The reservoir may be connected to the oxygenator heat exchanger through hoses and/or tubes. The heater/cooler may be connected to the reservoir by a thermal connecting element. Heating/cooling is exchanged between heater/cooler and the reservoir.

According to some embodiments, the system comprises an additional heat exchanger which is connected to the reservoir, the heater/cooler being connected to the additional heat exchanger for exchanging a quantity of heat.

Furthermore, the system may comprise a unit adapted for providing a fluid to the blood of the patient, in particular, a cardioplegic solution, and wherein the heater/cooler (14) is connected to the unit for providing the fluid and configured to heat or to cool said fluid. It follows that, in addition to the function of exchanging heat with the heat exchanger of the oxygenator and of warming or cooling a patient's blood in this way, the heater/cooler can fulfill the function of heating or cooling other fluids (such as a cardioplegic solution) used e.g. in a heart-lung machine.

In the case of all the above described embodiments, the heater/cooler may comprise a cooling module with a plurality of Peltier elements and a heating module without any Peltier elements. The heating module may comprise a heating coil. Since the capacity of Peltier elements is limited, the Peltier elements may thus be used exclusively for a cooling function. A heat exchanging medium stored in a reservoir (see above) can already be cooled or heated, prior to starting the actual operation, with the aid of the cooling module or the heating module.

In the following, embodiments of a device according to the present disclosure will be described. The embodiments described are to be regarded in any respect as being only illustrative and non-restrictive, and various combinations of the specified features are included in the present disclosure.

DETAILED DESCRIPTION

Figure 1:
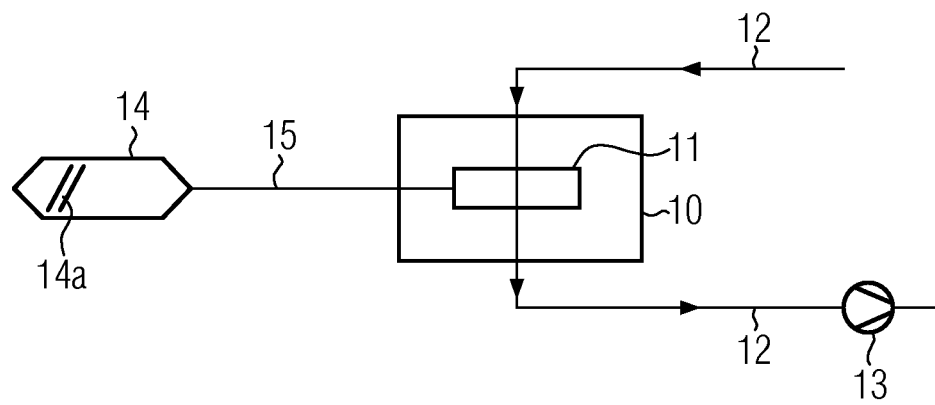
FIG. 1 is a diagram illustrating a system comprising an oxygenator, which includes a heat exchanger and a thermoelectric heater/cooler with Peltier elements, according to embodiments of the disclosure.

FIG. 1 is a diagram illustrating a schematic representation of a system, according to embodiments of the present disclosure. The system comprises an oxygenator 10 with a heat exchanger 11. The blood of a patient is circulated via the lines 12 and the oxygenator 10 with the aid of a pump unit 13. The blood is oxygenated in the oxygenator 10 and cooled or warmed, as required, with the aid of the heat exchanger 11. The system shown in FIG. 1 may be part of a heart-lung machine, an extracorporeal membrane oxygenation (ECMO) device or a minimized extracorporeal circulation (MECC) device, which may comprise numerous additional elements, as known from the prior art. The oxygenator 10 may be a membrane oxygenator.

A thermoelectric heater/cooler 14 is connected to the heat exchanger 11 via a thermal connecting element (contact element) 15. The thermal connecting element 15 may comprise a thermally highly conductive metal. A transfer of heat between the heat exchanger 11 of the oxygenator 10 and the heater/cooler 14 takes place directly via the thermal connecting element 15 without any liquid heat exchanging medium being required.

In embodiments, the heater/cooler 14 comprises Peltier elements 14a, which allow a substantially maintenance-free operation.

Figure 2:
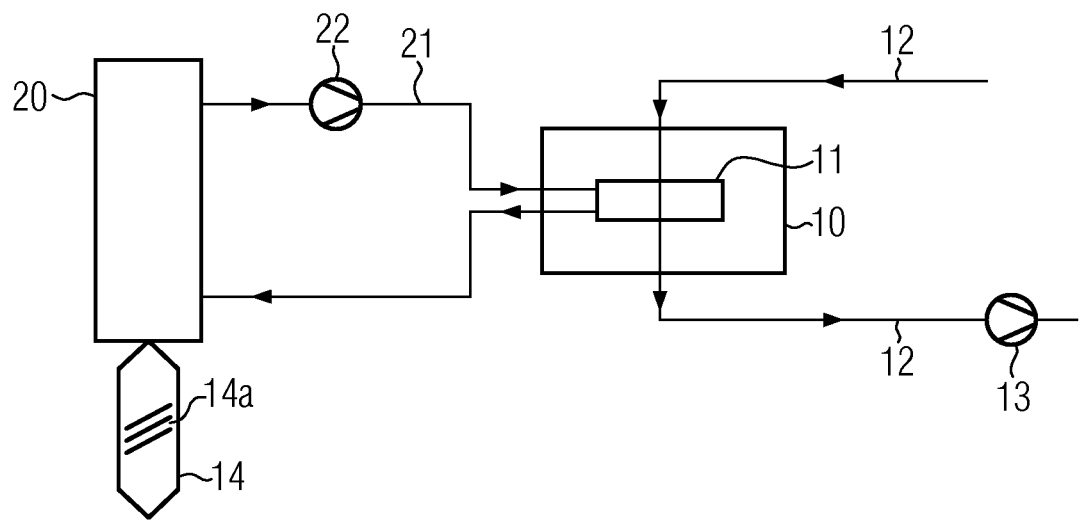
FIG. 2 is a diagram illustrating a system comprising an oxygenator, which includes a heat exchanger and a thermoelectric heater/cooler with Peltier elements, said thermoelectric heater/cooler heating or cooling via a thermal connecting element and a heat exchanging medium stored in a reservoir, according to embodiments of the disclosure.
Figure 3:
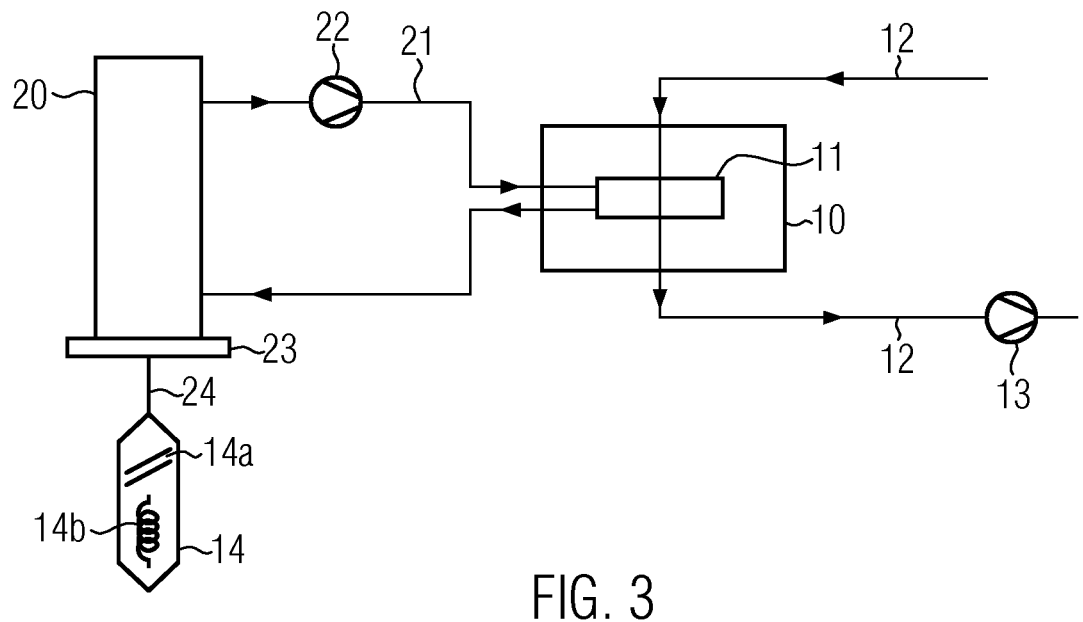
FIG. 3 is a diagram illustrating a system comprising an oxygenator, which includes a heat exchanger and a thermoelectric heater/cooler with Peltier elements, said thermoelectric heater/cooler heating or cooling via a heat exchanger and a heat exchanging medium stored in a reservoir, according to embodiments of the disclosure.

Additional exemplary embodiments are illustrated in FIG. 2 and FIG. 3. Elements corresponding to those shown in FIG. 1 are designated by like reference numerals. The systems shown in FIG. 2 and FIG. 3 comprise an oxygenator 10 with a heat exchanger 11. The oxygenator 10 may be a membrane oxygenator with membranes produced e.g. from polypropylene or polyethylene. The heat exchanger 11 may be a spiral tube made of stainless steel or it may comprise a plurality of hose sections.

The blood of a patient is circulated via the lines 12 and the oxygenator 10 with the aid of a pump unit 13. The blood is oxygenated in the oxygenator 10 and cooled or warmed, as required, with the aid of the heat exchanger 11. The systems shown in FIG. 2 and FIG. 3 may be part of a heart-lung machine, an extracorporeal membrane oxygenation (ECMO) device or a minimized extracorporeal circulation (MECC) device. The oxygenator 10 may be a membrane oxygenator.

A heat exchanging medium is supplied from a reservoir 20 via lines 21 with the aid of a pump unit 22 to the heat exchanger 11 of the oxygenator 10, and, when an exchange of heat with the blood in the patient's extracorporeal blood circulation has taken place, it is returned from said heat exchanger 11 to the reservoir 20. The heat exchanging medium may e.g. be water or glycerine. In embodiments shown in FIG. 2, a thermoelectric heater/cooler 14 is connected directly to the reservoir 20 for heating or cooling the heat exchanging medium.

The thermoelectric heater/cooler 14 may, for example, be arranged in or on the reservoir 20. Embodiments shown in FIG. 3 differ from those shown in FIG. 2 insofar as, for heating or cooling the heat exchanging medium stored in the reservoir 20, a further heat exchanger 23 is used, which is connected to a heater/cooler 14 via a thermal connection 24. In embodiments shown in FIG. 3, the heater/cooler 14 comprises a cooling module with Peltier elements 14a and a heating module with a heating coil. These modules may also be provided in the embodiments shown in FIG. 1 and FIG. 2.

The embodiments shown in FIGS. 2 and 3 can be obtained by suitably retrofitting existing conventional systems, or completely new systems may be formed. Advantageously, these embodiments comprise thermoelectric heaters/coolers 14, in particular heaters/coolers with Peltier elements, thus allowing a substantially maintenance-free, reliable operation as regards the heater/cooler 14. Through the lines 21, a heat exchanging medium is, however, circulated via the heat exchanger 11 of the oxygenator 10, and this entails the risk of contamination of the blood to be oxygenated, if the circuit of the heat exchanging medium is not air tight (i.e. closed to the atmosphere). This risk is avoided in the case of the embodiments shown in FIG. 1. In point of fact, the prejudice that the heat exchanger 11 of the oxygenator 10 could only be operated via a heat exchanging medium existed in the prior art, but it turns out that a direct heat transfer via a thermal connecting element without the use of a heat exchanging medium is possible for reliably cooling or warming the blood of an extracorporeal blood circulation.

Furthermore, the heater/cooler 14 according to the above described embodiments can be used for heating or cooling fluids other than the patient's blood. For example, a cardioplegic solution, which is administered for protecting or sedating the cardiac muscle, can be heated or cooled by means of the heater/cooler 14.

The invention claimed is:

1. A system for extracorporeal blood circulation, comprising:
   an oxygenator which includes a heat exchanger configured for warming or cooling blood in the extracorporeal blood circulation of a patient, and
   a heater/cooler configured for exchanging a heat quantity with the heat exchanger,
   wherein the heater/cooler comprises a cooler including a plurality of Peltier elements and a separate heater, wherein the separate heater consists of at least one heating coil and does not include any Peltier elements, wherein all Peltier elements are exclusively involved with a cooling function, and
   wherein the heater/cooler is connected to the heat exchanger by a thermal connecting element.

2. A system for extracorporeal blood circulation, comprising:
- an oxygenator which includes a heat exchanger configured for warming or cooling blood in the extracorporeal blood circulation of a patient,
- a heater/cooler configured for exchanging a heat quantity with the heat exchanger, and
- a reservoir configured for storing a heat exchanging medium and connected to the heat exchanger,
- wherein the heater/cooler comprises a cooler disposed outside the reservoir and including a plurality of Peltier elements and a separate heater, wherein the separate heater consists of at least one heating coil and does not include any Peltier elements, wherein all Peltier elements are exclusively involved with a cooling function, and
- the heater/cooler is connected to the reservoir and configured to heat or cool the heat exchanging medium, stored in the reservoir and circulated through the heat exchanger.

3. The system according to claim 2, wherein the heater/cooler is connected to the reservoir by a thermal connecting element.

4. The system according to claim 2, wherein the heater/cooler is connected to the reservoir by a further heat exchanger.

5. The system according to claim 2, wherein the reservoir is connected to the heat exchanger through hoses and/or tubes.

6. The system according to claim 5, further comprising a pump connected to the tubes.

7. The system according to claim 2, further comprising a unit adapted for providing a fluid to the blood of the patient, in particular, a cardioplegic solution, and wherein the heater/cooler is connected to the unit for providing the fluid and configured to heat or to cool said fluid.

8. The system according to claim 2, wherein the system is or comprises a heart-lung machine, an extracorporeal membrane oxygenation (ECMO) device or a minimized extracorporeal circulation (MECC) device.

9. A system for extracorporeal blood circulation, comprising:
- an oxygenator which includes a heat exchanger configured for warming or cooling blood in the extracorporeal blood circulation of a patient,
- a heater/cooler configured for exchanging a heat quantity with the heat exchanger, wherein the heater/cooler comprises a cooler including a plurality of Peltier elements and a separate heater, wherein the separate heater consists of at least one heating coil and does not include any Peltier elements, wherein all Peltier elements are exclusively involved with a cooling function, and
- a thermal connecting element connected between the thermoelectric heater/cooler and the heat exchanger, the thermal connecting element comprising a thermally conductive metal for transferring heat between the thermoelectric heater/cooler and the heat exchanger such that no liquid heat exchanging medium passes between the thermodynamic heater/cooler and the heat exchanger.

10. The system according to claim 9, wherein the system is or comprises a heart-lung machine, an extracorporeal membrane oxygenation (ECMO) device or a minimized extracorporeal circulation (MECC) device.

* * * * *